(12) United States Patent
Odon (10) Patent No.: US 10,238,423 B2
(45) Date of Patent: Mar. 26, 2019

(54) DEVICE FOR EXTRACTING ELEMENTS FROM CAVITIES, WHICH USES A BAG FOR EXTRACTION AND AN APPLICATOR

(75) Inventor: Jorge E. Odon, Banfield (AR)

(73) Assignee: AIR BAG ONE SARL, Charles de Gaulle (LU)

( * ) Notice: Subject to any disclaimer, the term of this patent is extended or adjusted under 35 U.S.C. 154(b) by 89 days.

(21) Appl. No.: 14/123,453

(22) PCT Filed: May 31, 2012

(86) PCT No.: PCT/ES2012/070409
§ 371 (c)(1),
(2), (4) Date: Mar. 10, 2014

(87) PCT Pub. No.: WO2012/164139
PCT Pub. Date: Dec. 6, 2012

(65) Prior Publication Data
US 2014/0188126 A1    Jul. 3, 2014

(30) Foreign Application Priority Data

Jun. 2, 2011    (AR) .......................... AR20110101902

(51) Int. Cl.
*A61B 17/42*    (2006.01)
*A61B 17/22*    (2006.01)
(Continued)

(52) U.S. Cl.
CPC ............ *A61B 17/42* (2013.01); *A61B 17/442* (2013.01); *A61B 2017/00287* (2013.01); *A61B 2017/22034* (2013.01)

(58) Field of Classification Search
CPC ....... A61B 17/50; A61B 17/42; A61B 17/442; A61B 2017/00287; A61B 2017/22034; A61B 2017/22032
(Continued)

(56) References Cited

U.S. PATENT DOCUMENTS 1,162,516 A    11/1915 Richmond
1,782,714 A    11/1930 Davidson
(Continued)

FOREIGN PATENT DOCUMENTS

AR    058534 A1    2/2008
AR    060105329 A1    2/2008
(Continued)

OTHER PUBLICATIONS

Supplementary European Search Report dated Jul. 29, 2011 in a corresponding European Patent Application No. 08805389.7.
(Continued)

*Primary Examiner* — Diane Yabut
*Assistant Examiner* — Majid Jamialahmadi
(74) *Attorney, Agent, or Firm* — Sughrue Mion, PLLC (57) ABSTRACT

A device to extract elements contained in cavities that uses a bag for their extraction that folds onto itself and an applier provided with an air chamber, which bag has pockets into which tentacles of the applier are introduced; and that is provided with means to pull from same; an applier that is comprised by a first piece called outer tube, that is hollow and of rigid material which, at its distal end, turns into at least two tentacles that allow its radial flexibility, and in its proximal end, means are provided to fix the second piece, called inner tube, which is a hollow tube, open at its ends, that slides into the body of the outer tube and that provides a funnel at its distal end. The device may have grade scale either on the tentacles, the inner tube as well as on the bag. Additionally, this provides two rings used as reference, on each of the folds of the bag.

10 Claims, 5 Drawing Sheets

(51) Int. Cl.
*A61B 17/00* (2006.01)
*A61B 17/44* (2006.01)

(58) Field of Classification Search
USPC ......... 606/122–124, 119, 113; 294/183, 185, 294/186, 189, 86.4; 604/279
See application file for complete search history.

(56) References Cited

U.S. PATENT DOCUMENTS

| | | | |
|---|---|---|---|
| 1,782,814 A | 11/1930 | Froehlich | |
| 2,637,320 A | 5/1953 | Greenberg | |
| 2,863,305 A * | 12/1958 | Shepherd | C09K 5/00 106/162.81 |
| 3,168,092 A | 2/1965 | Silverman | |
| 3,310,166 A * | 3/1967 | Mauthe | B65D 29/00 206/459.1 |
| 3,664,328 A * | 5/1972 | Moyle, Jr. | A61B 10/0291 600/569 |
| 3,982,544 A | 9/1976 | Dyck | |
| 4,243,040 A | 1/1981 | Beecher | |
| 4,469,100 A | 9/1984 | Hardwick | |
| 4,875,482 A * | 10/1989 | Hariri | A61B 17/42 606/122 |
| 5,312,385 A | 5/1994 | Greco | |
| 5,417,684 A * | 5/1995 | Jackson | A61B 17/00234 606/1 |
| 5,505,738 A * | 4/1996 | Hempel | A61B 17/14 30/504 |
| 5,527,282 A | 6/1996 | Segal | |
| 5,593,413 A | 1/1997 | Alexander | |
| 5,910,146 A * | 6/1999 | Alexander | A61B 17/442 606/119 |
| 5,935,136 A * | 8/1999 | Hulse | A61B 17/442 606/119 |
| 6,077,278 A * | 6/2000 | Mayer | A61B 17/06061 606/139 |
| 6,270,505 B1 | 8/2001 | Yoshida et al. | |
| 6,398,790 B1 | 6/2002 | Alexander | |
| 6,695,791 B2 | 2/2004 | Gonzalez | |
| 6,846,029 B1 | 1/2005 | Ragner et al. | |
| 7,658,747 B2 | 2/2010 | Forde | |
| 9,247,958 B2 | 2/2016 | Odon | |
| 2002/0013601 A1 | 1/2002 | Nobles et al. | |
| 2004/0015175 A1 | 1/2004 | Nguyen | |
| 2005/0072695 A1 * | 4/2005 | Shaanan | A63B 55/00 206/315.3 |
| 2009/0254096 A1 * | 10/2009 | Porat | A61B 5/0011 606/123 |
| 2010/0241134 A1 * | 9/2010 | Odon | A61B 17/22032 606/123 |
| 2010/0292724 A1 * | 11/2010 | Ravikumar | A61B 17/221 606/185 |
| 2011/0196382 A1 * | 8/2011 | Barrier | A61B 17/442 606/123 |
| 2013/0304081 A1 * | 11/2013 | George | A61B 17/442 606/123 |

FOREIGN PATENT DOCUMENTS

| | | |
|---|---|---|
| AR | 062010 A3 | 8/2008 |
| CN | 1524499 | 9/2004 |
| DE | 19747822 A1 | 7/1999 |
| FR | 703402 A | 4/1931 |
| FR | 2450113 A2 | 9/1980 |
| GB | 1162516 A | 8/1969 |
| JP | 6217991 A | 8/1994 |
| WO | 93/17629 A1 | 9/1993 |
| WO | 9702785 A1 | 1/1997 |
| WO | 9803123 A1 | 1/1998 |
| WO | 0154568 A1 | 8/2001 |
| WO | 03002822 A1 | 1/2003 |
| WO | 2005025427 A1 | 3/2005 |
| WO | 2008068367 A1 | 6/2008 |
| WO | 2009013383 A1 | 1/2009 |
| WO | WO2009/013383 * 1/2009 | ............ A61B 17/42 |
| WO | 2009/101186 A1 | 8/2009 |

OTHER PUBLICATIONS

Official Action dated Jan. 30, 2012 in Eurasian Patent Application No. 201070178.
Hessburg et al., "An Assisted Obstetric Delivery Device for Resource-limited Settings," Intl. J. for Service Learning in Engineering 7:1-12, Fall 2012.
Patent Examination Report No. 1 issued in Australian Patent Application No. 2008278919 dated Nov. 20, 2012.
Notice of Reasons for Rejection issued in Japanese Patent Application No. 2010-517426 dated Oct. 9, 2012.
Chinese Office Action issued in Chinese Patent Application No. 200880025355.9, dated Jul. 6, 2011.
"Bag Definition"—Merriam-Webster Dictionary, accessed Jun. 9, 2014.
Official Action issued in Eurasian Patent Application No. 201070178, dated Jan. 31, 2015.
Written Opinion for PCT/EP2016/063220, dated Sep. 5, 2016.
International Search Report for PCT/EP2016/063220, dated Sep. 5, 2016.

* cited by examiner

FIG. 1A

CROSS SECTION AA

FIG. 1B

CROSS SECTION BB

DEVICE FOR EXTRACTING ELEMENTS FROM CAVITIES, WHICH USES A BAG FOR EXTRACTION AND AN APPLICATOR

This application is a U.S. national phase of International Application No. PCT/ES2012/070409, filed May 31, 2012, which claims the priority of Argentine Patent Application No. 20110101902, filed Jun. 2, 2011, the disclosures of which are incorporated herein by reference.

FIELD OF THE INVENTION

The present invention refers to a device to extract elements contained in a cavity, which allows to carry out the described extracting method that is claimed in patent application No. P060105329 filed in Argentina on Dec. 1, 2006 by the same inventor and in the improvement to said patent filed in Argentina as patent application No. P070103245 dated Jul. 20, 2007, also by the same inventor, and published as application PCT WO2009/013383 on Jan. 29, 2009.

The proposed device is preferably used in the assistance of births and/or extractions of elements located in cavities of the human body, to facilitate the work of medical professionals, although it may be used in other areas, such as in industrial fields.

In innumerable uses of the present invention, and such as the method of the mentioned patent application No. P060105329, we find applications in gastroenterology, in tasks such as: extraction of foreign rectal bodies, fecal obstructions, extraction of foreign gastroesophageal bodies and extraction of gallstones; in urology, in tasks such as extraction of urinary calculi, extraction of elements accidentally moved during medical instrumentation; in vascular surgery, in tasks such as: displacement of clots and/or vascular prosthesis or to revascularize noble territories; and finally in otolaryngology, in tasks such as: extraction of foreign bodies located in ears or nostrils and wax removal.

STATE OF THE ART OF THE INVENTION AND IMPROVEMENTS THEREON

In relation with the state of the art of the present invention and in particular in the field of peri-neonatology, we can mention tools and accessories presently used in deliveries, which are used at the time of birth, and among the mostly known ones are the "forceps"—vacuum devices—

Patent GB 1162516 in the name of Davis Ind. Equipment Co., published in August 1969 reveals a "Tube for deliveries" that comprises a double-wall bag with a chamber between the walls that allows to be inflated with a fluid, that provides support to provide longitudinal rigidity and means to introduce a fluid into said chamber. Said support comprises four arms joined at one of its ends to a ring, where opposite ends are free to open or to close with respect to said ring. These free ends provide greater surfaces to cover the greatest possible section of the circumference. From the description and the figures, it is seen that its function is to maintain the tube for deliveries open and to accompany the dimensions of the delivery channel and of the head of the fetus when introduced into the woman in labor. The tube is introduced into the woman in labor and remains inside her at all times up to the child's birth. The fetus enters in its entirety within the tube and is extracted by vacuum.

U.S. Pat. No. 4,875,482 in the name of Harari and others, granted in October 1989 reveals a "flexible grasping device" that comprises a flexible/elastic holding mesh in the form of a tube, with an end which diameter is feasible to be reduced after being introduced around the fetus' head and to adjust it round its neck. The mesh is structurally formed in such a way that as the traction force is applied along the longitudinal axis and the end is closed around the fetus' neck, when pulling same it pushes the fetus from its jaw and the back part of its head through the delivery channel.

U.S. Pat. No. 6,270,505 in the name of Yoshida and others, granted in August 2001 reveals a "bag for endoscopy with inflatable type opening and an instrument to insert the bag for endoscopy". This comprises a bag folded within a groove and it is introduced into a cavity; once in position, the bag is extracted from the groove and air is insuflated into a chamber peripherically provided in its end. A surgery tool introduced by said groove, preferably a surgery plier, takes the element to be extracted and enters same into said volume within the abdominal cavity. The volume is closed pulling from a strip, simultaneously with the deflation of the air chamber, with which the element to be extracted is wholly comprised within the volume of the bag. The purpose of the air chamber is to open the opening of the bag to place, with a tool, the element to be extracted within the bag. Yoshida creates a volume in the proximity of the element to be extracted, takes said element with a surgery plier and completely places it within said volume. It closes the open end of the bag with a strip, and simultaneously removes the air, leaving the element enclosed within the bag. Then, a pull from the groove takes place to extract the bag and element to be extracted from the abdominal cavity. Yoshida reveals an inflatable bag that has an air chamber around all the circumference of its end. The air chamber is, for Yoshida, of polygonal shape (see FIGS. 5 and 6) and preferably has from 4 to 6 sides. No reference is made to round bags. The fact that the bag be faceted is to provide rigidity to the inflated bag with a minimum pressure. The vertices of the faceted form provide a sufficient rigidity so as to create an open volume inside the patient's cavity on the side of the bag's opening. Yoshida reveals a higher rugosity to favor the location of the element to be extracted within the bag. The inventor wants to avoid that said element loosens when pulling the bag.

U.S. Pat. No. 5,910,146 of inventor Gary Alexander, granted in June 1999 reveals a "device to assist in deliveries". This device reveals an elongated arm made of a woven material, with an open end, which is folded to form an inner coat and an outer coat. A rope is provided along the elongated arm and forms a loop in the folded part of said arm, so as to close its open end. This invention also reveals an applier made by an applying rod, a handle, an insertion sleeve, a cone and a plurality of insertion rods. The plurality of insertion rods are loose with respect to the handle, so that when used they should have to be placed in the handle and be fixed by auxiliary means. Those rods are also provided with external hooks and butts to fix them to the handle and be able to operate the device.

The method revealed in application P060105329 is known to the inventor of the present invention, by means of which the extraction of at least one element contained in a cavity is performed as well as the device to carry out said method, preferably used in assisting deliveries and which particular structure allows a simple and non traumatic stage of the delivery. Said method is performed in the stages of: a) inserting within said cavity at least one flexible element capable of increasing its volume as a result of the entrance of a fluid, and in such a way that said element to be extracted be in superficial contact with the mentioned flexible element; b) introducing a fluid into said at least one flexible element until the surface of said at least one flexible element gets in contact with the inner wall of the recipient and of the element to be extracted; and c) getting hold of the at least one flexible element and pulling it toward the opening of the extraction of the cavity until its complete extraction. The device to perform this method is made up by at least one flexible element capable of increasing its volume as a result of an increase of the inner pressure of the contained fluid.

It was seen in experiments conducted with equivalent materials and elements that the use of said devices in deliveries gave rise to problems in the insertion of the bags into the uterine cavity, in particular when trying to surround the fetus' head. Said problems were timely studied and have been solved with Argentine patent application P 0701 03245 filed on Jul. 20, 2007.

Argentine patent application P 07 01 03245 is also known to the inventor of this present invention which application reveals a device to extract elements contained within a cavity, and that it is of preferable usage in assistance of deliveries and/or extraction of elements located in cavities of the human body, thus facilitating the task of medical professionals. Said device is made up by a bag having one of its ends open, through which it is possible to introduce the element to be extracted, wherein in a first preferred embodiment, it provides on the outer surface of the bag and along all the circumference at least one air chamber capable of getting in contact with the element to be extracted when receiving external pressure, being said chamber connected to a pressure generating means; and in a second embodiment, the device is defined on such bag with an outer fold, forming an annular cavity at the time it makes contact with the cavity containing the element to be extracted.

It is expected that the use of this present device may eliminate or reduce the use of forceps, plungers that generate vacuum (vacuum devices) and other aggressive means that so much risk caused when used in assistance to deliveries.

MAIN OBJECT OF THE PRESENT INVENTION

A first object of the present invention is to improve the asepsis of the inner parts of the bags which are introduced within cavities, in special in the vagina of women in labor. Folded bags are entered with the advancing edge open into the delivery channel with the aid of a spatula, used by sectors of the circumference. At this partial and graded introduction, there may be some contact between the mucous membrane of the vagina wall and the advancing edge of the folded bag. The present invention provides a closed advancing edge that, with the aid of an applier, does not open until said edge has passed the vagina of the woman in labor and reached the fetus' head.

Another object of the present invention is to facilitate the placement of the set inside the cavity and to make contact with the element to be extracted. Besides it has measure grades and visual references of the location of the bag with respect to the element to be extracted and to the cavity that contains same.

With the present invention, either fluids, specifically liquid antiseptics to avoid contagion of infections to the fetus before entering the delivery channel, as well as lighting video cameras, may be introduced.

The present invention may be of help to assistants in deliveries with lesser knowledge and/or skills than average devices of the previous state of the art did provide.

BRIEF DESCRIPTION OF FIGURES

In order to better understand the object of the present invention, schematic figures have been included, in its preferred embodiment, which figures have a descriptive nature, wherein.

In said figures, same references correspond to identical elements of the invention.

DETAILED DESCRIPTION OF THE INVENTION

Figure 1A:
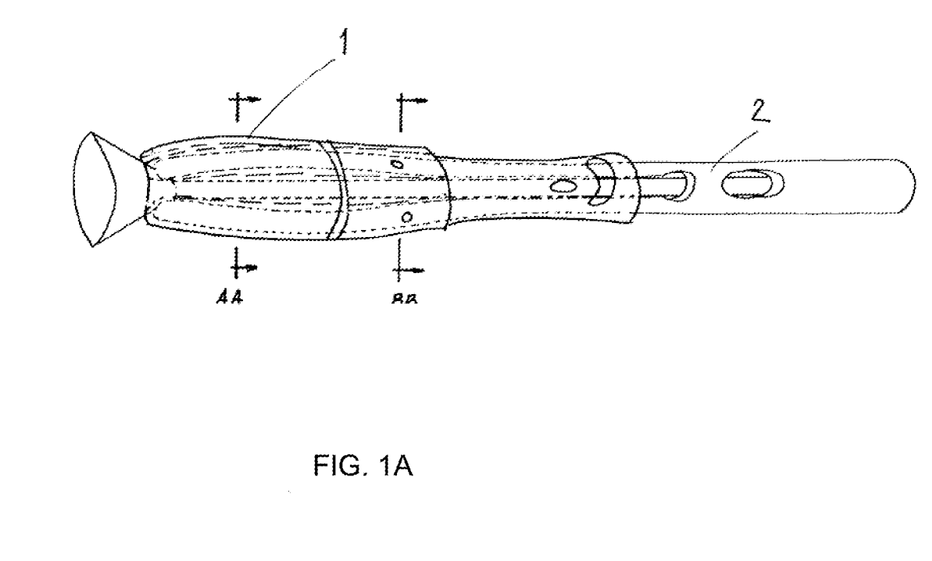
FIG. 1A shows a perspective view of the device to extract elements contained in a cavity with the applier inserted within the pockets of the bag.

In FIG. 1A there appears the device to extract elements contained in cavities, that uses a bag for their extraction and an applier, in a first preferred embodiment, to render assistance in deliveries. Same is made up by a bag 1 and an applier 2. The bag reveals some pockets and the applier some tentacles. The latter are inserted into the pockets and are preferably fixed with fasteners. In this way, the device is ready to be used.

Figure 1B:
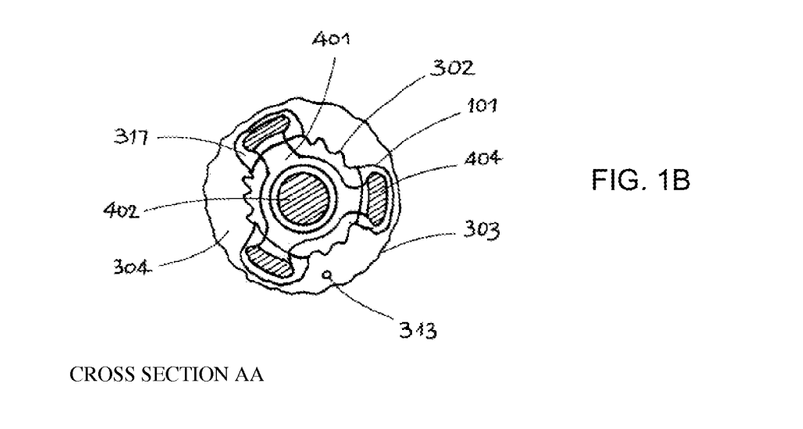
FIGS 1B and 1C show two cross sections AA and BB.

In FIG. 1B, the cross section AA is seen. The inner tube 302 and the outer tube 303 formed by the fold of the bag and that create a space 304 between both, are observed. Tentacles 404 are inserted into the pockets 317. These pockets are made up by an additional surface 101 which is added to the inner tube of the bag. Applier 401, inner tube 402 and the channel 313 are also seen.

Figure 1C:
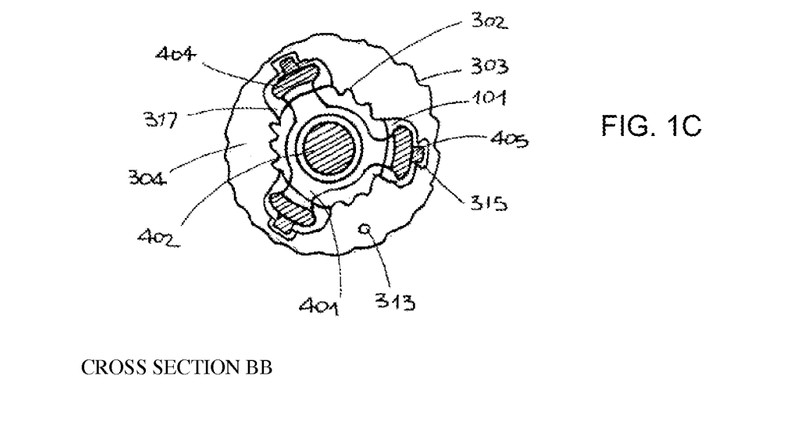

In FIG. 1C, the cross section BB is seen. The inner tube 302 and the outer tube 303 formed by the fold of the bag and that create a space 304 between both, are observed. Tentacles 404 are inserted into the pockets 317. These pockets are made up by an additional surface 101 which is added to the inner tube of the bag. Applier 401, inner tube 402 and channel 313 are also seen. Besides, it is observed that fasteners 405 are fixed to the tentacles while fasteners 315 are fixed to the additional surface 101.

Figure 2:
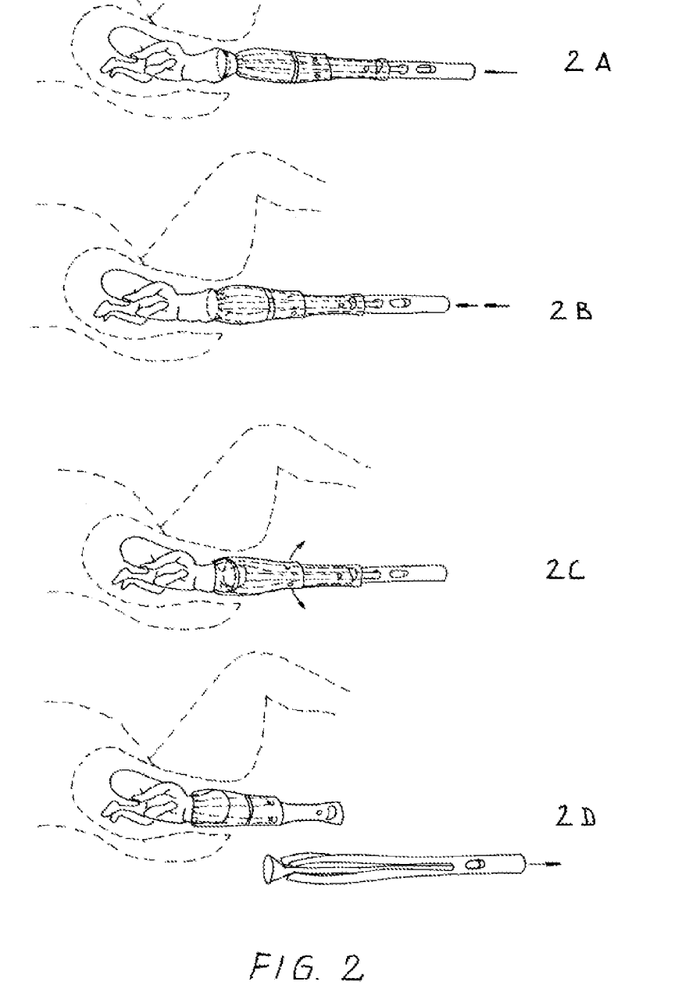
FIG. 2 illustrates the stages of fixing the device and of the removal of the applier.

In FIG. 2, the stages of fixing the device and of the removal of the applier are seen. In FIG. 2 A, the device has been introduced into the delivery channel and the funnel makes contact with the fetus' head. In FIG. 2 B, while further pushing the device towards the fetus, the funnel causes the tentacles to open. In FIG. 2 C, the device already completely surrounds the fetus' head and is ready to remove the applier once the fasteners fixing the bag to the applier are unfastened. In FIG. 2 D, it is seen that the bag has remained inside the delivery channel and is surrounding the fetus' head, and the applier has been removed.

Figure 3:
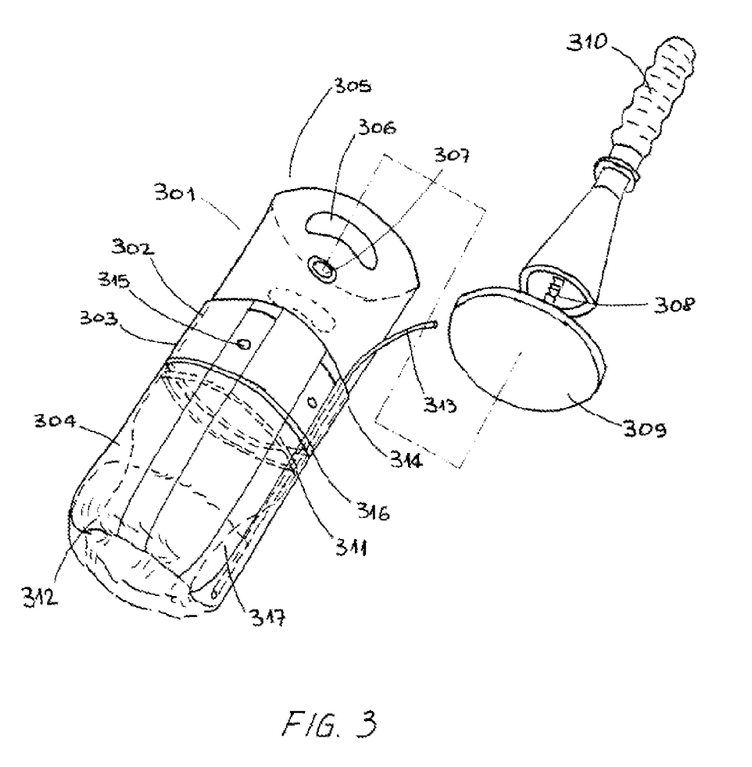
FIG. 3 illustrates a perspective view of the bag folded onto itself and of an extracting loop.

In FIG. 3, the bag is seen; this bag is an open tube 301 made of a flexible material, preferably transparent and wide enough so as to easily allow its folding to get adapted to the fetus' head and the delivery channel. To be used, the bag is folded onto itself near the centre, creating an inner tube 302 and an outer tube 303, with a space 304 in the middle. It is seen, at a first end 305 that it has at least two openworks 306 on its surface that work as handles at the time of pulling the device in a tractive manner. Further to the centre of the tube, two holds 307, preferably reinforced with metallic or rigid plastic ledges through which an axis 308 linked to a disc 309 of a traction handle 310 may pass, in a second tractive manner. Closer to the centre of the tube, a first ring of one color 311 is provided, which will work as a first reference for folding the bag. In the centre of the bag, an air chamber 312 is provided along all of its perimeter. Preferably, the air chamber, of toroidal shape, is welded to the tube by its inner diameter. The air chamber may be inflated and deflated by a conduct 313 which links it with the outside and which inflating and deflating means are not part of this present invention. In the second end of the bag 314, opposite to the first, a plurality of fasteners 315 are provided, which will fasten this end, once the bag is folded, to the applier as will be further seen. Closer to the centre, a second colored ring 316 is provided, which will work as a second reference for folding the bag and, preferably, will have a different color than that of the first colored ring. Toward the centre of the tube, a plurality of pockets 317 is provided, distributed on the perimeter of the bag. The opening 318 of said pockets is reinforced and aims at the direction of the second end of the tube while in the bottom of the pocket, it reaches the fold. The junction of the pockets to the tube is made with weldings, the latter may be reinforced and show rounded ledges. These pockets may be provided on the outer or inner side of the bag. Optionally, the bag may have a longitudinal grade scale, preferably as from the fold of same.

Figure 4:
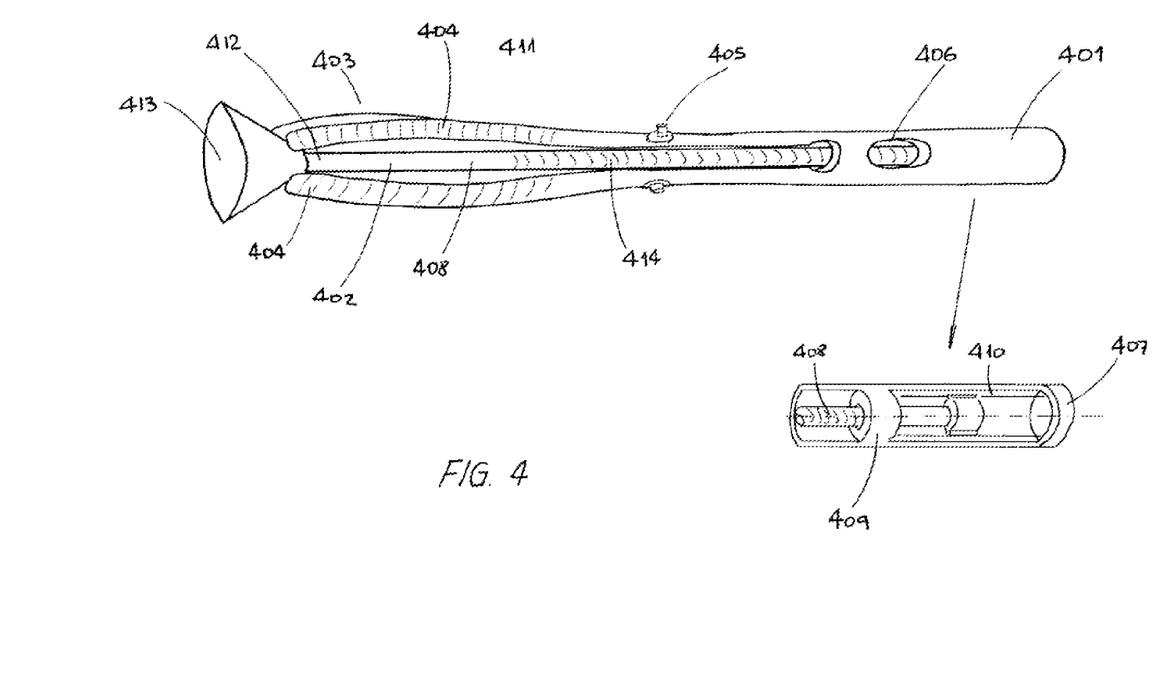
FIG. 4 illustrates a perspective view of the applier.

In FIG. 4, an applier is seen, which applier is comprised by two pieces: an outer tube 401 and an inner tube 402. The outer tube is a hollow tube, of rigid material, that, at its distal end 403, turns into at least two tentacles 404 or soft curved arms that allow their radial flexibility. On the body of each tentacle, a fastener 405 is provided. Close to the proximal end, an openwork window 406 is provided. The proximal end is closed with a threaded lid 407. In the inner diameter of the outer tube, on its body 408, a butt 409 and a groove 410 are provided to lock, both longitudinally as well as axially, the inner tube. Optionally, at least one of the tentacles shows a longitudinal scale 411. In one embodiment, one of the tentacles is longer than the rest. This is so since the fetus has its chin leaning on its chest, for which reason the distance of the back part of its head is lesser than the distance of the front part of same.

The inner tube is a hollow flexible tube that has at its distal end a flexible funnel 413. This tube is entered and slided along the interior of the outer tube. Optionally, it may provide a longitudinal scale 414. Along the interior of this tube, fluids, such as innocuous antiseptics or lubricants, may be provided. The funnel may provide holes in the way of a watering can so that the injected fluids may easily spread out and not be provided in an isolated point. A lighting video camera may also be inserted.

In the method of use in the preferred embodiment as assistance in deliveries, the set is formed folding the bag and introducing the tentacles into the pockets. Once inside, the bag is fixed to the applier, fixing its fasteners to those of the tentacles. In this way, the reference colored rings coincide and the funnel arises by the fold of the bag. This set is introduced into the vagina until the cone contacts the fetus' head. At this time, and if some tentacle has a longitudinal scale, it may be clearly determined how deep the fetus is in relation to the vulva. If the set is further introduced, tentacles are forced to open due to the funnel. This introductory covering movement is softer and even due to the presence of the applier. At this moment, it is read on the scale of the inner tube and through the openwork window, how deep the device has entered surrounding the cephalic pole.

Once this position is reached, the bag is unfastened of the tentacles and the applier is removed, leaving the bag in position, inside the woman in labor and around the fetus' head and with the reference rings in coincidence. The air chamber is inflated, by any means, creating the air plier and traction is made from the latter from the openworks acting as handles. In case of using another way of traction, the disc is introduced inside the bag, the holes are threaded with the axis of said disc and same is fixed to the traction handle.

References of rings or of a longitudinal scale on the bag indicate, at all times, the fetus' advance in relation to its initial position. Once the fetus has crowned, the bag alone loosens. Delivery continues by normal means.

Some fluid may be provided to the fetus' environment through the inner tube that leads to a bell. Preferably, the fluid is liquid antiseptics, but some lubricant innocous to the fetus may also be provided. A lighting video camera may also be inserted.

With the present invention, the following distances may be clearly, certainly and easily read:

Distance up to which the applier was introduced when same contacts the fetus' head, measured with the scale on a tentacle and taking the vulva as reference;

Distance up to which the bag was introduced over the fetus' head, measured on the scale of the inner tube; and Distance of advance of the fetus pulled by the bag, which is read from the scale on the bag or by the distance between reference rings.

The invention claimed is:

1. A device to extract elements contained in cavities, comprising:
   a bag with pockets and means to extract the bag from a cavity, wherein the bag is a tube of flexible transparent material that is folded onto itself at a fold, and comprises an air chamber adjacent to the fold between an outer portion of the bag and an inner portion of the bag that is configured to be inflated/deflated through a conduit,
   an applier with an advancement measuring indicator;
   wherein the air chamber is configured to reduce an inner circumference of the bag when the air chamber is inflated; and
   said applier comprises two pieces:
      a first piece comprising an outer tube, that is a hollow tube, of rigid material, which, at a distal end, transitions into at least two tentacles or soft curved arms that are flexible, and
      a second piece comprising an inner tube, that is a hollow tube with open ends, which slides inside the outer tube and includes a funnel at a distal end of the inner tube;
   wherein the outer tube has, at a proximal end, means for fixing the inner tube thereto, and
   wherein said pockets are shaped to receive the tentacles or the soft curved arms of the applier, and
   wherein the inner portion of the bag is configured to move relative to the outer portion of the bag during extraction.

2. The device to extract elements contained in cavities of claim 1, wherein said advancement measuring indicator comprises a scale on the inner tube and an open window in the outer tube that exposes the scale on the inner tube.

3. The device to extract elements contained in cavities of claim 1, wherein said bag includes a first reference ring on the outer portion of the bag and a second reference ring on the inner portion of the bag.

4. The device to extract elements contained in cavities of claim 1, wherein said pockets include fasteners near ends of each pocket that connect the bag to the applier.

5. The device to extract elements contained in cavities of claim 1, wherein at least one tentacle or soft curved arm has a different length than another tentacle or soft curved arm.

6. A device to extract elements contained in cavities, comprising:

a bag with pockets, and handles or holes to extract the bag from a cavity, wherein the bag is a tube of flexible transparent material and is folded onto itself at a fold, and comprises an air chamber adjacent to the fold between an outer portion of the bag and an inner portion of the bag that is configured to be inflated/deflated through a conduit, an applier with an advancement measurement indicator;

wherein the air chamber is configured to reduce an inner circumference of the bag when the air chamber is inflated; and said applier comprises two pieces:
- a first piece comprising an outer tube, that is a hollow tube, of rigid material, which, at its distal end, transitions into at least two tentacles or soft curved arms that are flexible; and
- a second piece comprising an inner tube, that is a hollow tube, open at ends of the inner tube, which slides inside the outer tube and includes a funnel at its distal end, wherein the outer tube has, at a proximal end, a chamber, and the inner tube has an enlarged portion at a proximal end that is located inside the chamber, and the chamber restricts a sliding range of the inner tube with respect to the outer tube by restricting a sliding range of the enlarged portion, and wherein said pockets are shaped to receive the tentacles or the soft curved arms of the applier, wherein the inner portion of the bag is configured to move relative to the outer portion of the bag during extraction.

7. The device to extract elements contained in cavities of claim 6, wherein said bag comprises a marking for indicating advancement of the element being extracted.

8. The device to extract elements contained in cavities of claim 7, wherein the marking is comprised of two markings, a first marking and a second marking, located at each side of the fold, such that upon extraction, the first marking and the second marking move relative to one another as a result of relative sliding movement of the outer portion of the bag folded over the inner portion of the bag.

9. The device to extract elements contained in cavities of claim 6, wherein said bag comprises two markings, a first marking on the inner portion of the bag and a second marking on the outer portion of the bag, and the markings coincide before extraction of an element.

10. The device to extract elements contained in cavities of claim 6, wherein said bag comprises two markings, a first marking on the inner portion of the bag and a second marking on the outer portion of the bag, and a relative distance between the markings indicates at all times a location of an element in a cavity to be extracted with respect to an initial position of the element.

* * * * *